US007355195B2

(12) United States Patent
Ivo

(10) Patent No.: US 7,355,195 B2
(45) Date of Patent: Apr. 8, 2008

(54) METHOD AND APPARATUS FOR ASSOCIATING PATIENT AND EXPOSURE RELATED DATA WITH A RADIATION IMAGE

(75) Inventor: Dirk Ivo, Boechout (BE)

(73) Assignee: Agfa Healthcare, Mortsel (BE)

( * ) Notice: Subject to any disclaimer, the term of this patent is extended or adjusted under 35 U.S.C. 154(b) by 79 days.

(21) Appl. No.: 11/079,640

(22) Filed: Mar. 14, 2005

(65) Prior Publication Data

US 2005/0236593 A1 Oct. 27, 2005

Related U.S. Application Data

(60) Provisional application No. 60/569,074, filed on May 7, 2004.

(30) Foreign Application Priority Data

Apr. 27, 2004 (EP) .................. 04101760

(51) Int. Cl.
*G03B 42/08* (2006.01)
*G01T 1/27* (2006.01)
*H05B 33/00* (2006.01)

(52) U.S. Cl. ............... 250/581; 250/370.09; 250/484.4
(58) Field of Classification Search ................ 250/581, 250/582, 583, 584, 370.09, 484.4
See application file for complete search history.

(56) References Cited

U.S. PATENT DOCUMENTS

| | | | | |
|---|---|---|---|---|
| 5,014,045 A | * | 5/1991 | Shimura et al. ............ 345/156 |
| 5,334,851 A | | 8/1994 | Good et al. |
| 5,757,021 A | * | 5/1998 | Dewaele ..................... 250/581 |
| 6,047,257 A | * | 4/2000 | Dewaele ..................... 704/270 |
| 6,271,536 B1 | | 8/2001 | Buytaert et al. |
| 6,339,502 B1 | * | 1/2002 | Itakura ....................... 359/589 |
| 6,762,429 B2 | * | 7/2004 | Aonuma ..................... 250/583 |
| 6,800,870 B2 | * | 10/2004 | Sayag ........................ 250/584 |
| 6,811,079 B1 | * | 11/2004 | Vraa et al. .................. 235/383 |
| 6,901,159 B2 | * | 5/2005 | Baertsch et al. ............ 382/132 |
| 6,910,626 B2 | * | 6/2005 | Walsh ........................ 235/380 |
| 6,945,713 B2 | * | 9/2005 | Vraa et al. .................. 396/511 |
| 7,095,034 B2 | * | 8/2006 | Haug et al. .............. 250/484.4 |
| 7,162,067 B2 | * | 1/2007 | Motoki ....................... 382/132 |
| 7,197,529 B2 | * | 3/2007 | Nakagawa et al. ......... 709/200 |
| 2005/0133745 A1 | * | 6/2005 | Haug et al. ................ 250/581 |
| 2006/0180776 A1 | * | 8/2006 | Exelmans et al. .......... 250/584 |
| 2007/0018125 A1 | * | 1/2007 | Fletcher-Heath et al. ... 250/581 |

FOREIGN PATENT DOCUMENTS

| EP | 0 727 696 A1 | 8/1996 |
|---|---|---|
| EP | 0 908 762 A1 | 4/1999 |

OTHER PUBLICATIONS

European Search Report for EP04101760 (Oct. 4, 2004).

* cited by examiner

*Primary Examiner*—David Porta
*Assistant Examiner*—Faye Boosalis
(74) *Attorney, Agent, or Firm*—Leydig, Voit & Mayer, Ltd.

(57) ABSTRACT

Patient identification data and/or exposure related data or a code uniquely identifying at least one of these data is transferred shortly before or during exposure to a radio-frequency tag or the like coupled to a radiation detector. Transfer may be executed through the intermediary of a reader/writer coupled to a source of radiation.

17 Claims, No Drawings

METHOD AND APPARATUS FOR ASSOCIATING PATIENT AND EXPOSURE RELATED DATA WITH A RADIATION IMAGE

CROSS-REFERENCE TO RELATED PATENT APPLICATIONS

This patent application claims the benefit of U.S. Provisional Patent Application No. 60/569,074, filed May 7, 2004, which is incorporated by reference. In addition, this application claims the benefit of European Application No. 04101760.9 filed Apr. 27, 2004, which is also incorporated by reference.

FIELD OF THE INVENTION

The present invention relates to radiography, computed radiography as well as digital radiography.

The invention more particularly relates to a method and a system for associating data such as identification data of a patient and/or data relating to an x-ray exposure with a radiographic image.

BACKGROUND OF THE INVENTION

In addition to classical radiography systems in which a radiographic image of a patient is recorded on radiographic hard copy film, computed radiography systems based on storage phosphor technology are nowadays commonly used.

In such a computed radiography system a cassette conveying a photo-stimulable phosphor screen is exposed to a radiation image of a body part of a patient.

All kinds of data to be associated with the image such as demographic data (patient name, gender, date of birth etc.) and data relating to the exposure such as mAs, kV etc. are entered in a workstation or are retrieved from a hospital information system or a radiology information system.

These data are then transferred onto an identification means which is coupled with the cassette. For example the data are written into an EPROM device which is provided on the cassette conveying the exposed phosphor screen or the data are transferred via radio-frequency transmission to a radio-frequency tag provided on the cassette.

The identified cassette conveying an exposed photo-stimulable phosphor screen is then fed into a read out apparatus (also referred to as a 'digitizer') where the identification data are read from the identification means and where the radiographic image which is stored in the phosphor screen is read out. The radiographic image is read out by scanning the exposed photo-stimulable phosphor screen with stimulating radiation and by converting the image-wise modulated light which is emitted by the screen upon stimulation into a digital signal representation of the radiographic image.

A radiographic study often comprises more than one radiographic image. For example a study of a hand comprises two or three images on different cassettes.

In such a case several cassettes each containing a photo-stimulable phosphor screen are exposed to a radiation image of the patient in different positions or to different body parts of the patient. Commonly the individual images part of a study are taken in sequence. Then the exposed cassettes are taken to the identification station where identification of the individual images is performed.

Alternatively identification of all cassettes is performed prior to exposure.

It is clear that this procedure might result in erroneous identification because different data are to be associated with exposed cassettes which contain different images but which on the outer side are indistinguishable.

It is also possible that the data which are associated with the cassette correspond with the intended circumstances, for example the intended or default settings of the X-ray source but which, due to various possible circumstances do not exactly represent the effectively applied radiation data.

Information and complaint studies have learnt that the identification procedure in radiology departments in which cassette based systems are used, is experienced as complex and error prone during every step of the workflow.

Still another problem is that there is no feed back to the operator whether the cassette intending for exposure has been properly erased and is thus free from image information before a new exposure is performed.

It is thus clear that correct association of all kinds of identification and exposure related data as well as feedback on the status of the screen within a cassette is a crucial part within the workflow of a radiology department which influences the efficiency of operations within the radiography department.

Apart from computed radiography systems digital radiography systems are gaining importance. In such a system a digital radiography detector such as a Cmos based x-ray detector is exposed to a radiation image and a digital signal representation of the image is directly generated. The signal can then be applied to a hard copy recorder, a work station or a picture archiving system (PACS). Also in this type of systems adequate and error proof association of identification and exposure data and feedback of the status of the detector (exposed, ready for exposure etc.) is required.

It is an aspect of the present invention to provide a method and apparatus that overcomes the above-mentioned problems associated with the prior art workflow.

SUMMARY OF THE INVENTION

The above-mentioned aspects are realized by a method as set out in claim 1.

Another aspect of the invention relates to a system as set out in the appending claims. The system comprises a workstation arranged for entering patient identification data and/or exposure related data, a radiation detector, an electronic identification means coupled with said detector and a source of radiation provided with a reader/writer device arranged for communicating said data or a code uniquely identifying said data with said workstation and with said electronic identification means.

The radiation detector for example comprises a photo-stimulable phosphor screen or a digital radiography detector.

An example of an electronic identification means is a radio-frequency tag or the like enabling data communication from and towards the identification station (occasionally via the intermediary of a reader/writer device coupled to the source of radiation).

Specific features for preferred embodiments of the invention are set out in the dependent claims.

Further advantages and embodiments of the present invention will become apparent from the following description.

DETAILED DESCRIPTION OF THE INVENTION

While the present invention will hereinafter be described in connection with preferred embodiments thereof, it will be understood that it is not intended to limit the invention to those embodiments.

A first embodiment relates to a computed radiography system in which an x-ray image is recorded on a photo-stimulable phosphor screen conveyed in a cassette.

Identification data pertaining to the patient and/or exposure settings are entered in an identification station which is a workstation running an identification software.

More specifically these data are demographic data and exposure-related data such as patient's name, examination type, sub-examination type, exposure settings etc.

Alternatively these data are retrieved from a hospital information system or a radiology information system.

An erased cassette is positioned—for example in a bucky—in an adequate position for exposure to an x-ray image of a patient body part. The cassette comprises a radio-frequency tag such as has been described in European patent application EP 727 696.

Preferably prior to exposure feedback is provided from the cassette to the identification station on the status of the cassette: erased or non-erased.

It is possible to make the subsequent work flow dependent on the communicated status, e.g. to disable exposure of a non-erased cassette.

Next the source of radiation is activated in accordance with the settings entered in the identification station and the photo-stimulable phosphor screen is exposed to a radiation image of a body part of the patient.

During or short after exposure, in any case between the moment when the first action initiating the exposure is performed and the moment on which the radiation source and the detector can again be relatively displaced (shortly after exposure) the final data which were entered into the identification station are transferred to the tag on the cassette conveying the photo-stimulable phosphor screen. In other words these data are transferred to the tag on the cassette while it is in the exposure position.

Data transfer is preferably performed from identification station to cassette through the intermediary of a reader/writer mounted on or coupled to the radiation tube (for example be integrated in the collimator).

In this way correct identification data and actual exposure data are transferred to the cassette conveying the phosphor screen on which the image is to be recorded to which these data pertain so that erroneous identification or erroneous association of data and images are eliminated.

The above-described reader/writer is for example a reader writer based on Psion Tektronic technology or the like.

The transfer of data from the identification station (also called modality workstation) to the reader could be based on an explicit and/or exposure command.

It can either be achieved in a wireless way or via cable connection. The information by the reader towards a tag provided on the exposed cassette is a wire-less transfer.

The effective data can be transferred. However, in an alternative embodiment a code pertaining to the effective data can be transferred.

The cassette which now carries the radiation image as well as the exposure and identification data or a code pertaining to these data can then be removed from its position (e.g. from the bucky) and can be transferred to a read out apparatus where the image is read out and a digital representation is obtained and where also the data from the identification tag are read.

In this work flow image data and identification and exposure data are automatically associated with each other so that errors or wrong association of image and respective data are eliminated.

The digital signal representation of the radiation image and the identification and exposure data can then be applied to a hard copy recorder, a work station and/or archive station etc.

The above-described procedure relates to a computed radiography system based on a photo-stimulable phosphor screen detector.

In an alternative embodiment the detector is a digital radiography detector comprising a radiation sensor such as a sensor based on Cmos, Selenium or CCD technology or the like.

The above-described way of transferring data to the cassette in both the computed radiography and the digital radiography system ensures correct mapping or association of all data in the X-ray room pertaining to the patient and the exposure without an additional cassette identification step added to the work flow which would decrease the speed of operation.

I claim:

1. A method of associating data with a radiographic image, which image is carried on a radiation detector, comprising transferring at least one of patient identification data and exposure related data or a code uniquely identifying at least one of said data from an identification station to an identification means coupled to said radiation detector in the period of time between exposure of a patient to obtain said radiographic image and a subsequent relative displacement of a source of radiation used to obtain said radiographic image and said radiation detector.

2. A method according to claim 1 wherein at least one of said patient identification data and exposure related data or a code uniquely identifying said data is transferred from said identification station onto a reader/writer coupled to said source of radiation and from said reader/writer onto said identification means coupled to said detector.

3. A method according to claim 2 wherein said identification means comprises a radio-frequency tag coupled to a cassette conveying said detector.

4. A method according to claim 3 wherein said detector comprises a photo-stimulable phosphor screen.

5. A method according to claim 4 wherein said detector comprises a digital radiography detector.

6. A method according to claim 1 wherein said identification means comprises a radio-frequency tag coupled to a cassette conveying said detector.

7. A method according to claim 6 wherein said detector comprises a photo-stimulable phosphor screen.

8. A method according to claim 7 wherein said detector comprises a digital radiography detector.

9. A method according to claim 1 wherein said detector comprises a photo-stimulable phosphor screen.

10. A method according to claim 1 wherein said detector comprises a digital radiography detector.

11. A radiography system comprising:
   a workstation arranged for entering patient identification data and/or exposure related data,
   a radiation detector capable of carrying a radiographic image of a patient,
   an electronic identification means coupled with said detector, and
   a source of radiation provided with a reader/writer device arranged for communicating said data or a code uniquely identifying said data with said workstation and with said electronic identification means,
   wherein the data communication with said electronic identification means is performed in the period of time between exposure of a patient to obtain a radiographic image and a subsequent relative displacement of a source of radiation used to obtain said radiographic image and said radiation detector.

12. A radiography system according to claim 11 wherein said radiation detector comprises a photo-stimulable phosphor screen.

13. A radiography system according to claim 12 wherein said radiation detector comprises a digital radiography detector.

14. A radiography system according to claim 13 wherein said electronic identification means comprises a radio-frequency tag.

15. A radiography system according to claim 12 wherein said electronic identification means comprises a radio-frequency tag.

16. A radiography system according to claim 11 wherein said radiation detector comprises a digital radiography detector.

17. A radiography system according to claim 11 wherein said electronic identification means comprises a radio-frequency tag.

* * * * *